United States Patent [19]

Current

[11] Patent Number: 4,614,832

[45] Date of Patent: Sep. 30, 1986

[54] DIALKYL OXALATES FROM CARBON MONOXIDE AND AN ALCOHOL

[75] Inventor: Steven P. Current, Novato, Calif.

[73] Assignee: Chevron Research Company, San Francisco, Calif.

[21] Appl. No.: 104,333

[22] Filed: Dec. 17, 1979

[51] Int. Cl.$^4$ .............................................. C07C 67/36
[52] U.S. Cl. ................................... 560/204; 502/155; 502/213; 502/230; 560/190
[58] Field of Search ......................................... 560/204

[56] References Cited

U.S. PATENT DOCUMENTS

| | | | |
|---|---|---|---|
| 3,393,136 | 7/1968 | Fenton et al. | 560/204 |
| 3,994,960 | 11/1976 | Yamazaki et al. | 560/204 |
| 4,005,128 | 1/1977 | Zehner et al. | 560/204 |
| 4,005,129 | 1/1977 | Zehner | 560/204 |
| 4,005,130 | 1/1977 | Zehner | 560/204 |
| 4,076,949 | 2/1978 | Zehner | 560/204 |
| 4,118,589 | 10/1978 | Cassar et al. | 560/204 |

FOREIGN PATENT DOCUMENTS 2814708 10/1979 Fed. Rep. of Germany ...... 560/204

OTHER PUBLICATIONS

Rivetti et al, Journal of Organometallic Chemistry, 154 (1978) 323-6 (Jul., 1978).
Fenton et al, J. Org. Chem., 39(5), pp. 701-704 (1974).

*Primary Examiner*—Natalie Trousof
*Assistant Examiner*—Vera C. Clarke
*Attorney, Agent, or Firm*—J. A. Buchanan, Jr.; C. J. Caroli

[57] ABSTRACT

Preparation of dialkyl oxalates by the oxidative carbonylation of alcohols which comprises reacting carbon monoxide with an alcohol in the presence of a catalytic amount of a catalyst comprising palladium in complex combination with a ligand and in the presence of a stoichiometric amount of a quinone. Advantageously, carboxylic acid cocatalysts may be employed in addition to the palladium-containing catalyst.

12 Claims, No Drawings

4,614,832

1

DIALKYL OXALATES FROM CARBON MONOXIDE AND AN ALCOHOL

BACKGROUND OF THE INVENTION

This invention is concerned with an improved process for the oxidative carbonylation of alcohols to produce dialkyl oxalates and comprises the reaction of carbon monoxide with an alcohol in the presence of a catalytic amount of a catalyst comprising palladium in complex combination with a ligand and in the presence of a stoichiometric amount of a quinone, such as benzoquinone.

The preparation of dialkyl oxalate esters by the reaction of carbon monoxide and alcohol is well known. U.S. Pat. No. 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. Water scavengers or dehydrating agents such as alkyl orthoformic acid esters must be added to the liquid phase to prevent the accumulation of water.

In an article by Donald M. Fenton and Paul J. Steinwand, Journal of Organic Chemistry, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A recent West German Pat. No. 2,213,435 discloses a method for the synthesis of oxalic acid or oxalate esters using water or alcohol respectively. A platinum group metal salt, a salt of a metal more electropositive than the platinum group metal, e.g. copper (II) chloride and an alkali metal salt such as lithium chloride comprise the catalyst. Oxygen in stoichiometric amounts was employed as the oxidant. A disadvantage of such reaction is that explosive mixtures of oxygen and carbon monoxide are necessary to effect reaction. Alcohol conversion of less than 5 percent are obtained. Under non-explosive conditions only trace amounts of oxalate can be obtained.

U.S. Pat. No. 3,994,960 describes a process for the production of dialkyl oxalates by reacting an aliphatic alcohol with CO and oxygen under pressure in the presence of a catalyst of a mixture of a salt of a metal from the platinum group and a salt of copper or iron and a reaction accelerator including nitrates, sulfates, bicarbonates, carbonates, tertiary amines and hydroxides and carboxylates of alkali metals and alkaline earth metals, pyridine, quinoline, urea and thiourea. Conversion of the alcohol employed to the dialkyl oxalates in such process is low, generally less than 9 mole percent.

In a process similar to that of U.S. Pat. No. 3,994,960 above, West German Offenlegungschrift No. 2,601,139 shows the production of oxalic acid or its alkyl esters by reacting aliphatic alcohols or water with oxygen and carbon monoxide in the presence of palladium salts, redox salts and an amine or ammonia base.

U.S. Pat. Nos. 4,005,128 and 4,005,129 are concerned with the oxidative carbonylation of alcohols with carbon monoxide carried out in the presence of stoichiometric quantity of a metal oxide, such as copper or iron and a catalytic amount of a metal, such as palladium, platinum, copper, etc., and in the presence of an amine or an amine plus amine salt respectively.

U.S. Pat. No. 4,005,130 is concerned with a process for the preparation of oxalate esters by the oxidative carbonylation of alcohols with carbon monoxide in the presence of a catalytic amount of copper, nickel, cadmium, cobalt or zinc metal salt catalyst and at least a stoichiometric amount of an unsubstituted or halogen-substituted 2,5-cyclohexadiene-1,4-dione(1,4-benzoquinone). High yields and selectivity of the oxalate ester, over the carbonate ester and $CO_2$, are obtained and maximized by regulating temperature, carbon monoxide pressure and metal salt catalyst and by maintaining substantially anhydrous conditions.

U.S. Pat. No. 4,076,949 claims a process for the preparation of oxalate esters by reacting an alcohol with a mixture of carbon monoxide and oxygen in the presence of a catalytic mixture of:

(a) a palladium, rhodium, platinum, copper, or cadmium metal salt compound or mixture thereof;

(b) an aliphatic, cycloaliphatic, aromatic or heterocyclic amine or ammonium;

(c) a copper (I), copper (II), iron (II) or iron (III) oxidant salt compound; and (d) an ammonium or substituted ammonium salt compound or acid with a counterion other than a halide.

Alternatively, a ligand or coordination complex compound of the metal salt compound may be employed.

U.S. Pat. No. 4,118,589 relates to a process for producing oxalic acid and esters of oxalic acid. More particularly, this patent describes a catalytic process for preparing oxalic acid and esters of same by the oxidative reaction, in a liquid phase, of carbon monoxide and water or alcohols with oxygen in the presence of redox systems. The catalyst systems used in accordance with the teaching of the patent comprise a redox catalyst consisting essentially of a salt of Pd (II) and salts of a metal more electropositive than Pd having at least two oxidation states and, optionally, salts of alkaline metals, and co-catalytic amounts of at least one base having the formula $R_3N$ in which the groups R, which may be like or unlike, are selected from the group consisting of hydrogen and alkyl radicals having from 1 to 10 carbon atoms.

The liquid oxalate esters are solvents, but the preferred use is as feedstock for hydrogenation to ethylene glycol.

SUMMARY OF THE INVENTION

The present invention provides a superior process for the production of dialkyl oxalates by the oxidative carbonylation of a normally liquid alcohol with carbon monoxide in the presence of (1) a catalytic amount of a catalyst comprising palladium in complex combination with a ligand and (2) at least a stoichiometric amount of a quinone oxidant under mild reaction conditions of temperature and pressure such as to effect reaction of the alcohol and carbon monoxide to produce dialkyl dioxide.

In accordance with the invention, the production of dialkyl oxalates in high yields and better selectivity is effected by carrying out the reaction of alcohol and carbon monoxide in the conjoint presence of a catalyst comprising palladium in complex combination with a ligand and a stoichiometric amount of a quinone, at a reaction temperature below about 100° C. and above about 25° C. and a reaction pressure of below about 1200 psi; and above about 500 psi. Yield and selectivity are further improved by the use of a catalytic amount of a carboxylic acid as part of the catalyst system.

DESCRIPTION OF THE INVENTION

As hereinbefore mentioned, the present invention is based on the discovery that superior yields of dialkyl oxalates at better selectivities can be obtained from the reaction of an alcohol and carbon monoxide in the presence of a palladium-containing catalyst, with or without a carboxylic acid as cocatalyst, and a quinone oxidant. Reaction conditions of temperature and pressure are less severe than those encountered in the prior art. Further, the conjoint use of quinone oxidant and palladium catalyst is critical. Pursuant to the invention, a minimum amount of byproduct carbonate is formed, and yields of the order of 90-100 mol percent dialkyl oxalate based on quinone oxidant, can be obtained.

When quinone oxidant is used with catalysts other than palladium catalysts, yields and selectivities are much lower. This is shown in U.S. Pat. No. 4,005,130, Example 1, where yields of diethyl oxalate and of byproduct diethylcarbonate were 41.5% and 10.8%, respectively. Similarly, when a palladium catalyst is used with an oxidant other than a quinone, yields and selectivities are also lower compared with yield and selectivity obtained pursuant to the present invention. Thus, U.S. Pat. No. 4,005,128 shows in the best Example 24, a yield for diisopropyl oxalate of 81%, and a yield for diisopropyl carbonate of 2.4%. Moreover, in both the aforesaid examples more severe reaction conditions than those of the present invention were used. Thus, the temperature in both examples was 125° C., and the pressure 1600 and 1800 psi, respectively.

The palladium-containing catalyst herein contemplated is formed by complexing a palladium source and a ligand using known methods, as described, for example, in U.S. Pat. No. 4,005,128, mentioned above and herein incorporated by reference.

Thus, suitable palladium sources for complexing include the palladium (II) compounds, for example palladium (II) sulfate, nitrate, carboxylates, such as acetate, propionate and oxalate; the palladium (II) halides, such as the chloride, bromide and iodide. Palladium compounds of valence state other than +2 are also suitable. Examples include tetrakis(triphenylphosphine)palladium (0), tris(dibenzylideneacetone)dipalladium (0), bis(triphenylphosphine)(1,4-benzoquinone)palladium (0). As indicated, palladium metal as such can also be used. Preferred are the palladium (II) carboxylates.

The ligands are triorgano compounds of phosphorus, arsenic, antimony, or nitrogen. Suitable ligands include alkyl phosphines such as trimethylphosphine and tributylphosphine, aryl-phosphines such as triphenylphosphine, mixed alkylaryl phosphines such as diethylphenylphosphine, trialkylamines, such as triethylamine or 1,4-diamino-bicyclo[2.2.2]octane. Phosphites, such as triphenyl phosphite or tributyl phosphite may also be employed. Other suitable ligands include tetramethyl diphosphinoethane and tetraphenyl diphosphinoethane, as well as phosphorus-substituted polymers such as polymer-bound triphenyl phosphine on styrene-divinylbenzene copolymers. Exactly analogous derivatives of arsenic and antimony may be used; however, because of their greater ease of preparation and stability of the derived complexes, the derivatives of phosphorus are preferred.

The complex palladium compounds suitable for use in the process of the present invention may contain in the molecule, in addition to the ligands discussed above, one or more other atoms, groups or molecules, which are chemically bonded to the palladium atom or atoms. Atoms which may be bonded to the metal include, for example, hydrogen, nitrogen and halogen atoms; groups which may be bonded to the palladium include, for example, hydrocarbyl, hydrocarbyloxy, carbonyl, nitrosyl, cyano and $SnCl_3$—groups, molecules which may be bonded to the palladium include, for example, organic isocyanides and isothiocyanates.

Examples of suitable complex compounds are those represented by the following formulae:

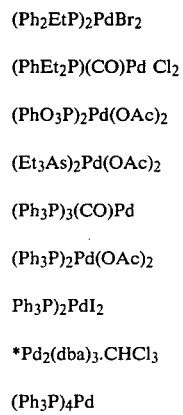

*dba=dibenzylideneacetone

The complex compounds employed may be introduced into the reaction mixture as such, or they may be formed in situ from a palladium source noted above and the desired ligand.

As hereinbefore mentioned, a cocatalyst carboxylic acid may be used in amounts of 1 to 50 mols per mol of palladium. The carboxylic acid may be mono- or polycarboxylic acid containing from 1-20 carbon soluble in the reaction medium. Preferred examples are the lower mono carboxylic acids of from 1-6 carbons such as acetic or propionic acid. Also preferred is oxalic acid.

The quinone oxidant employed in accordance with the invention is a cyclic diketone capable of being reduced to aromatic diols. It may be represented by the formula

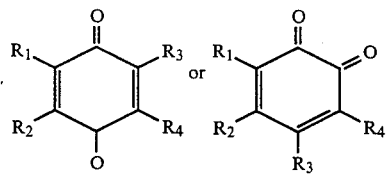

wherein $R_1$, $R_2$, $R_3$, and $R_4$ can be hydrogen, alkyl, aryl, halogen, alkoxy, or cyano, and wherein $R_1$ and $R_2$ or $R_3$ and $R_4$ can be connected to form an aromatic ring, provided that the total number of carbon atoms in the quinone does not exceed about 20. Specific examples of quinone oxidants are 1,4-benzoquinone and halogen-substituted 1,4-benzoquinones, including the mono-, di-, tri- and tetra-substituted chloro, bromo, fluoro and iodo compounds. In addition to 1,4-benzoquinone per se, representative halogen-substituted 1,4-benzoquinones include, for example, 2-chloro, 2-bromo-, 2-fluoro and 2-iodo-1,4-benzoquinones, 2,5-, 2,6- and 2,3-dichloro-, dibromo, difluoro-, and diiodo-1,4-benzoquinone, 2,3,5-trichloro-, tribromo-, trifluoro-, and triiodo-1,4-benzoquinones and the 2,3,5,6-tetrachloro-1,4-benzoquinone(chloranil), 2,3,5,6-tetra-bromo-1,4-benzoquinone(bromanil), 2,3,5,6-tetrafluoro- and 2,3,5,6-tetraiodo-1,4-benzoquinones. Additional examples are 1,4-naphthaquinone, 1,2-naphthaquinone, diphenoquinone, phenanthraquinone, 1,2-benzoquinone, 2,3,5,6-tetracyano-1,4-benzoquinone, 2,3,5,6-tetramethyl-1,4-benzoquinone. Mixtures of the quinones may also be employed. In the reaction the substituted or unsubstituted 1,4-benzoquinones are converted to the corresponding diol, e.g., 1,4-benzenediol (hydroquinone) which may be reoxidized to the dione for recycle and reuse in the oxidative carbonylation process of the invention. The preferred oxidant is 1,4-benzoquinone. In the reaction the quinone employed in at least a stoichiometric amount, functions as an oxidant and a proton acceptor.

The alcohols suitable for use in the process of the present invention and generally employed in at least stoichiometric quantities, are the monohydric saturated aliphatic and alicyclic alcohols and may contain other substituents such as halo, amido, alkoxy, amino, carboxy, cyano, etc. radicals in addition to the hydroxyl group. The substituents, in general, do not interfere with the reaction of the invention. The alcohols which may be primary, secondary or tertiary alcohols conform to the general formula ROH, wherein R is an optionally substituted aliphatic or alicyclic group preferably containing from 1 to 20 carbon atoms. In general, the satisfactory alcohol is one which is normally liquid under the conditions employed in the carbonylation reaction. Representative alcohols especially suitable for use in this invention are monohydric alcohols such as methyl, ethyl, n-, iso-, sec-, and tert-butyl, amyl, hexyl, octyl, lauryl, n- and sec-propyl, cetyl, benzyl, chlorobenzyl and methoxybenzyl alcohols as well as, for example, cyclohexanol, octanols, heptanols, decanols, undecanols, 2-ethyl hexanol, nonanol, myristyl alcohol, stearyl alcohol, methyl cyclohexanol, pentadecanol, oleyl and eicosonyl alcohols, and the like. Preferred alcohols are the normally liquid monohydric alcohols having 1 to 6 carbon atoms.

The reaction between the alcohol, carbon monoxide, and oxidant may be carried out in an autoclave or any other high pressure reactor. A general procedure is to charge the alcohol, catalyst, and the oxidant into the reactor vessel, introduce the proper amount of carbon monoxide to obtain the desired reaction pressure and then heat the mixture at the desired temperature for the appropriate period. The reaction can be carried out batchwise or as a continuous process and the order of addition of the reactants may be varied to suit the particular apparatus employed. The reaction products are recovered and treated by any conventional method such as distillation and/or filtration, etc. to effect separation of the oxalate from unreacted materials, catalyst, oxidant, byproducts, etc. The reaction is performed and takes place under relatively anhydrous conditions.

The catalysts employed are in the homogeneous state in the reaction mixture at reaction conditions.

The reaction is generally carried out in the presence of a catalytic proportion of the palladium catalyst and will proceed with small amounts of the catalyst compounds hereinabove described. Generally the proportions of the catalyst used in the reaction will be equivalent to between about 0.001 to 5 mols of palladium in the palladium-containing catalyst per 100 mols of quinone and are preferably used in amounts between about 0.01 to 2 mols of palladium per 100 mols of quinone. Larger or smaller amounts may be employed at varied pressures or reaction rates. When carboxylic acid cocatalyst is used, the amount will range from about 1 to 50 mols, preferably 5 to 25 mols per mol of palladium.

The process of the invention is operated entirely under the liquid phase conditions of the anhydrous alcohol, oxidant and catalyst. Although not required, solvents, if desired, which are chemically inert to the components of the reaction system may be employed. Suitable solvents include, for example, hydrocarbons such as hexane, heptane, octane, toluene and xylene; ethers, such as tetrahydrofuran, diethylether; halogenated hydrocarbons, such methylene chloride, chloroform and dichlorobenzene; organic esters, such as ethyl acetate, n-propyl formate, isopropyl acetate, sec- and iso-butyl acetate, amyl acetate, cyclohexyl acetate, n-propyl benzoate, lower alkyl phthalates, etc. The preferred method of operation is with excess alcohol used with the carbonylation reaction, functioning also as a solvent.

As indicated above the reaction can be suitably performed by introducing the carbon monoxide at a desired pressure into contact with the alcoholic reaction medium containing the specified reactants, catalysts and oxidant and heating to the desired temperature. In general, carbon monoxide pressures of about 500 psi to about 1200 psi preferably 800 to 1000 psi may be employed as total reaction pressure. Excess quantities of carbon monoxide are generally employed. A suitable recycle of the carbon monoxide may be employed. The reaction will proceed at temperatures of from about 25° C. to 100° C. It is generally preferred to operate the process at temperatures in the range of 35° C. to 80° C. to obtain a convenient rate of reaction. Heating and/or cooling means may be employed interior and/or exterior of the reaction to maintain the temperature within the desired range.

The reaction time is generally dependent upon the alcohol being reacted, temperature, pressure and on the amount and type of catalyst and oxidant being charged as well as the type of equipment being employed. Reaction times will vary dependent on whether the process is continuous or batch. The reaction is limited by the available oxidant, alcohol and carbon monoxide.

The following examples are provided to illustrate the invention in accordance with the principles of this invention but are not to be construed as limiting the invention in any way except as indicated by the appended claims.

EXAMPLES

Example 1

An 11 ml stainless steel microreactor was charged with:
palladium acetate (7.1 mg, 0.03 mmol);
triphenyl phosphine (23.9 mg, 0.09 mmol);
1,4-benzoquinone (324 mg, 3.0 mmol);
diglyme, (213 mg, 1.6 mmol);
methanol (2.33 g, 31 mmol).

The reactor was sealed and 1000 psi carbon monoxide added. The reactor was heated at 65° C. and shaken for 1 hour. After cooling and releasing the gases, quantitative gas chromatography using the diglyme as an internal standard indicated the presence of dimethyl oxalate (295 mg, 2.5 mmol) in 83% yield, and dimethyl carbonate (1.8 mg, 0.02 mmol) in 0.7% yield.

Example 2

A 300 ml stainless steel autoclave was charged with:
palladium acetate (56.6 mg, 0.25 mmol);
triphenyl phosphine (197 mg, 0.75 mmol);
1,4-benzoquinone (5.411 g, 50.1 mmol);
dodecane (867 mg, 5.09 mmol);
isobutyl alcohol (100 ml).

The reactor was sealed, flushed once with nitrogen, and 1000 psi carbon monoxide added. The reaction mixture was stirred at 1600 rpm and heated to 60° C. Samples were withdrawn periodically and analyzed by quantitative gas chromatography using dodecane as internal standard:

| Time | Isobutyl Carbonate | Isobutyl Oxalate |
| --- | --- | --- |
| 0.5 hr | 0.6 mmol, 1.2% | 14.1 mmol, 28.1% |
| 1.0 hr | 0.9 mmol, 1.8% | 20.1 mmol, 40.1% |
| 1.5 hr | 1.1 mmol, 2.2% | 24.4 mmol, 48.7% |
| 2.5 hr | 1.2 mmol, 2.4% | 26.1 mmol, 52.1% |
| 4.5 hr | 1.4 mmol, 2.8% | 30.7 mmol, 61.3% |

After 5.5 hrs the reactor was cooled. The pressure was released through a tube filled with Ascarite for the determination of carbon dioxide. A weight gain of 24 mg (0.55 mmol, 1.1%) was noted.

Example 3

Three 11 ml stainless steel microreactors were each charged with:
palladium acetate (4.5 mg, 0.020 mmol);
triphenyl phosphine (15.9 mg, 0.061 mmol);
1,4-benzoquinone (108.0 mg, 1.0 mmol);
methanol (972.0 mg, 30.4 mmol);
dodecane (18.6 mg, 0.109 mmol);
methylene chloride (4 ml).

The reactors were sealed and 1000 psi carbon monoxide added. After shaking at 80° C. for 4 hrs, the reactors were cooled and the gases vented. Quantitative gas chromatography using dodecane as an internal standard indicated that dimethyl oxalate had been formed in an average yield of 95.7%. No dimethyl carbonate was observed. Treatment of the reaction solution with excess ferric sulphate in water resulted in the near quantitative recovery of 1,4-benzoquinone.

The following three examples (4, 5, and 6) were stopped short of completion for comparison of respective yields in the presence of acetic acid or various solvents.

Example 4

An 11 ml stainless steel microreactor was charged with:
palladium acetate (2.0 mg, 0.009 mmol);
triphenyl phosphine (7.3 mg, 0.028 mmol);
1,4-benzoquinone (194.4 mg, 1.80 mmol);
acetic acid (5.4 mg, 0.09 mmol);
diglyme (123.7 mg, 0.92 mmol);
methanol (1.8 ml).

The reactor was sealed and 1000 psi carbon monoxide added. After 1 hr. at 38° C. with shaking, the reaction was stopped for comparison. After cooling and releasing the gases, quantitative gas chromatography indicated the formation of dimethyl oxalate (157.1 mg, 1.33 mmol) in 74% yield. Only a trace of dimethyl carbonate was observed.

Comparative Example

The above reaction was repeated with the exception that no acetic acid was included. The yield of dimethyl oxalate was 44%, and a trace of dimethyl carbonate was found.

Example 5

Five 11 ml stainless steel microreactors were each charged with:
palladium acetate (2.0 mg, 0.009 mmol);
triphenyl phosphine (7.3 mg, 0.028 mmol);
1,4-benzoquinone (194.4 mg, 1.80 mmol);
diglyme (147.6 mg, 1.10 mmol)
methanol (1.8 ml).

Acetic acid was added according to the Table. The reactors were sealed and 1000 psi carbon monoxide added. The reactor was heated at 38° C. and shaken. After 1 hour the reactions were stopped for comparison.

After cooling and releasing the gases, quantitative gas chromatography using diglyme as the internal standard indicated the presence of dimethyl oxalate in the amounts shown in the Table.

| Acetic Acid-Charged | Dimethyl Oxalate Formed |
| --- | --- |
| 1. 0, 0 | 0.78 mmol, 43.3% |
| 2. 2.7 mg, 0.045 mmol | 1.00 mmol, 55.6% |
| 3. 5.4 mg, 0.090 mmol | 1.30 mmol, 72.2% |
| 4. 13.5 mg, 0.225 mmol | 1.63 mmol, 90.6% |
| 5. 27.0 mg, 0.450 mmol | 1.55 mmol, 86.1% |

In all cases, no more than a trace of dimethyl carbonate was produced.

Example 6

Five 11 ml stainless steel microreactors were charged with:
palladium acetate (6.7 mg, 0.03 mmol);
triphenyl phosphine (23.6 mg, 0.09 mmol);
1,4-benzoquinone (324.0 mg, 3.0 mmol);
methanol (480.0 mg, 15.0 mmol).

Solvents were added as shown in the Table. The reactors were changed with 1000 psi carbon monoxide and heated at 65° C. with shaking. After 1 hour, the reactants were stopped for comparison. Quantitative gas chromatography using diglyme as an internal standard indicated dimethyl oxalate and benzoquinone in the amounts shown in the Table.

| Solvent | Dimethyl Oxalate | Recovered Benzoquinone |
| --- | --- | --- |
| n-Hexane, 3 ml | 56.4% | 5.6% |
| Toluene, 3 ml | 42.4% | 12.3% |
| Tetrahydrofurane, 3 ml | 22.2% | 43.7% |
| Methylene chloride, 3 ml | 52.2% | 8.1% |
| Methanol, 3 ml | 83.2% | 1.5% |

Example 7

Five 11 ml stainless steel microreactors were each charged with:
palladium acetate (4.5 mg, 0.02 mmol);
triphenyl phosphine (15.7 mg, 0.06 mmol);

methanol (960 mg, 30.0 mmol);
dodecane (35.3 mg, 0.21 mmol);
methylene chloride (4 ml).

Quinones were added as noted in the Table. The reactors were sealed and 1000 psig carbon monoxide added. After shaking at 80° C. for 4 hours, the reactors were cooled and the gases released. Quantitative gas chromatography using dodecane as internal standard indicated the presence of dimethyl oxalate as noted in the Table.

| Quinone Charged | Yield of Dimethyl Oxalate |
| --- | --- |
| 1. 1,4-Benzoquinone (110.0, 1.02 mmol) | 100% |
| 2. Quinhydrone (217.8 mg, 1.00 mmol) | 68.7% |
| 3. 2,3,5,6-Tetrachloro-1,4-benzoquinone (246.0 mg, 1.01 mmol) | 61.8% |
| 4. 1,4-Naphthoquinone (158.7 mg, 1.00 mmol) | 8.4% |
| 5. 1,2-Naphthoquinone (158.6 mg, 1.00 mmol) | 70.2% |

What is claimed is:

1. A process for preparing dialkyl oxalates by the oxidative carbonylation reaction which comprises contacting a normally liquid monohydric saturated aliphatic or alicyclic alcohol containing from 1 to 20 carbon atoms with carbon monoxide in the presence of (1) a catalytic amount of a catalyst comprising palladium in complex combination with a ligand and (2) at least a stoichiometric amount of a quinone, said contacting being conducted at a reaction temperature above about 25° C. and below about 100° C., and a reaction pressure above about 500 psi and below about 1200 psi, said reaction being carried out substantially in the absence of oxygen.

2. A process according to claim 1, wherein the catalyst is present in an amount equivalent to about 0.001 to 5 mols of palladium per 100 mols of quinone.

3. A process according to claim 2, wherein the catalyst is present in an amount of about 0.01 to 2 mols of palladium per 100 mols of quinone.

4. A process according to claim 1 wherein there is present a carboxylic acid cocatalyst which is a mono- or polycarboxylic acid containing from 1 to 20 carbon atoms soluble in the reaction medium, in an amount of 1 to 50 mols per mol of palladium contained in the catalyst comprising palladium.

5. A process according to claim 4 wherein the carboxylic acid cocatalyst is a monocarboxylic acid of 1 to 6 carbon atoms or oxalic acid.

6. A process according to claim 5 wherein the carboxylic acid cocatalyst is present in an amount equivalent to about 5 to 25 mols per mol of palladium.

7. A process for preparing dialkyl oxalates by the oxidative carbonylation reaction which comprises contacting a normally liquid monohydric saturated aliphatic or alicyclic alcohol containing from 1 to 20 carbon atoms and carbon monoxide at a temperature above about 25° C. and below about 100° C., and a pressure of above about 500 psi and below 1200 psi, in the presence of (1) a catalytic amount of a catalyst comprising palladium in complex combination with a triorgano compound of phosphorus, arsenic, antimony or nitrogen, and (2) at least a stoichiometric amount of a quinone oxidant, said reaction being carried out substantially in the absence of oxygen.

8. A process according to claim 7 wherein the catalyst is present in an amount equivalent to about 0.001 to 5 mols of palladium per 100 mols per quinone.

9. A process according to claim 8 wherein the catalyst is present in an amount equivalent to about 0.01 to 2 mols of palladium per 100 mols of quinone.

10. A process according to claim 8 wherein there is present a carboxylic acid cocatalyst which is a mono- or polycarboxylic acid containing from 1 to 20 carbon atoms soluble in the reaction medium in an amount of about 1 to 50 mols per mol of palladium.

11. A process according to claim 10, wherein the carboxylic acid cocatalyst is present in a monocarboxylic acid of 1 to 6 carbon atoms or oxalic acid and is present in an amount of about 5 to 25 mols per mol of palladium.

12. A process according to claim 11 wherein the palladium containing catalyst is present in an amount equivalent to about 0.01 to 2 mols of palladium per 100 mols of quinone.

* * * * *